(12) United States Patent
Klaassen et al.

(10) Patent No.: US 8,267,860 B2
(45) Date of Patent: *Sep. 18, 2012

(54) VAGINAL SPECULUM

(75) Inventors: Bernhard Wilhelm Gaziena Nicolaas Klaassen, Huissen (NL); Rita-Helene Holseng Klaassen, Huissen (NL)

(73) Assignee: Comfortpat B.V., Huissen (NL)

( * ) Notice: Subject to any disclaimer, the term of this patent is extended or adjusted under 35 U.S.C. 154(b) by 367 days.

This patent is subject to a terminal disclaimer.

(21) Appl. No.: 12/637,054

(22) Filed: Dec. 14, 2009

(65) Prior Publication Data

US 2010/0094095 A1    Apr. 15, 2010

Related U.S. Application Data

(62) Division of application No. 10/451,066, filed as application No. PCT/NL00/00949 on Dec. 22, 2000, now Pat. No. 7,658,712.

(30) Foreign Application Priority Data

Dec. 24, 1999 (NL) .................................... 1013958

(51) Int. Cl.
    *A61B 1/32* (2006.01)

(52) U.S. Cl. ............................ 600/220; 600/222

(58) Field of Classification Search .......... 600/219–225, 600/241, 245, 184; 606/119
    See application file for complete search history.

(56) References Cited

U.S. PATENT DOCUMENTS

| | | | |
|---|---|---|---|
| 2,545,201 A | | 3/1951 | Gilbert |
| 3,075,516 A | | 1/1963 | Strauch |
| 3,324,850 A | | 6/1967 | Gunning et al. |
| 3,736,919 A | | 6/1973 | Cotey |
| 3,769,968 A | | 11/1973 | Blount et al. |
| 3,769,980 A | | 11/1973 | Karman |
| 4,010,740 A | | 3/1977 | Littorin |
| 4,385,626 A | | 5/1983 | Danz |
| 4,971,036 A | | 11/1990 | Collins |
| 5,052,372 A | | 10/1991 | Sahpiro |
| 5,072,720 A | | 12/1991 | Francis |
| 5,167,222 A | | 12/1992 | Schinkel et al. |
| 5,329,938 A | | 7/1994 | Lonky |
| 5,465,709 A | | 11/1995 | Dickie et al. |
| 5,873,820 A * | 2/1999 | Norell ........................ 600/220 |
| 6,004,265 A * | 12/1999 | Hsu et al. ..................... 600/223 |
| 6,024,696 A | | 2/2000 | Hoftman et al. |
| 7,311,663 B2 * | 12/2007 | Marcotte ..................... 600/222 |
| 7,658,712 B2 * | 2/2010 | Klaassen et al. ............. 600/220 |

FOREIGN PATENT DOCUMENTS

| | | |
|---|---|---|
| DE | 74 364 C | 4/1893 |
| GB | 2341320 | 3/2000 |

* cited by examiner

*Primary Examiner* — Pedro Philogene
(74) *Attorney, Agent, or Firm* — Sughrue Mion, PLLC

(57) ABSTRACT

A speculum for internal examination of a body cavity such as a vagina, comprising at least two spoons, each comprising a spoon blade that can be inserted in the body cavity, which spoons are attached to one another via a hinge pin and are hingeable between a closed position in which the spoon blades are essentially in contact with one another and a spread position in which the spoon blades are some distance apart, and at least one operating handle which is located outside the body cavity during use, a body rest being provided which, in conjunction with the operating handle, effects spreading of the spoon blades.

20 Claims, 4 Drawing Sheets

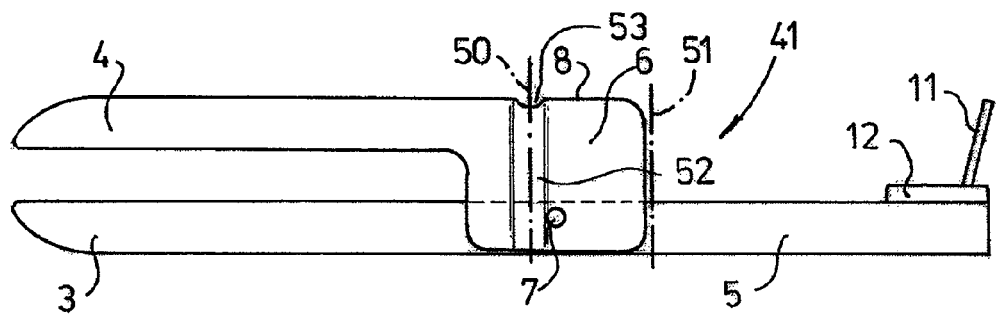
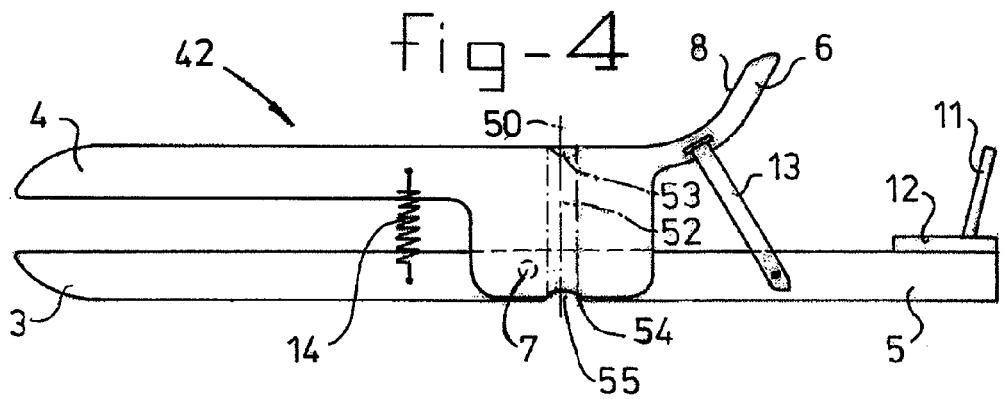
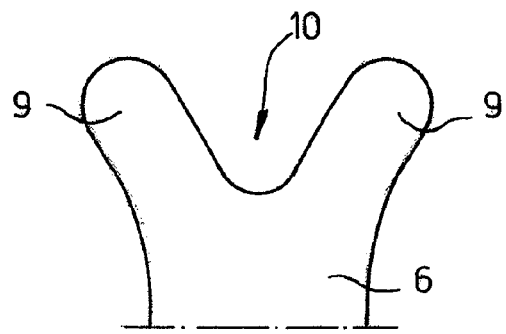

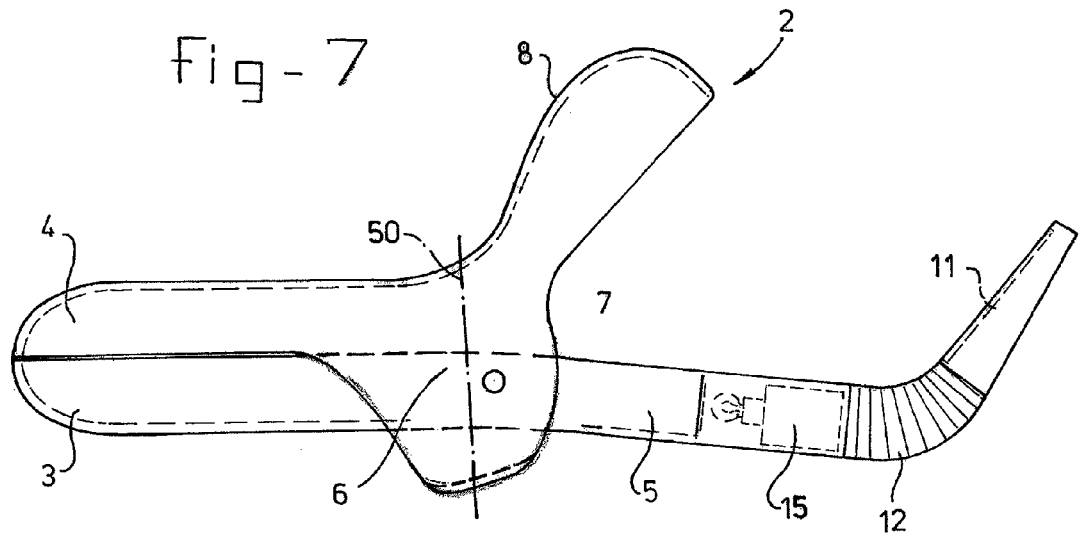
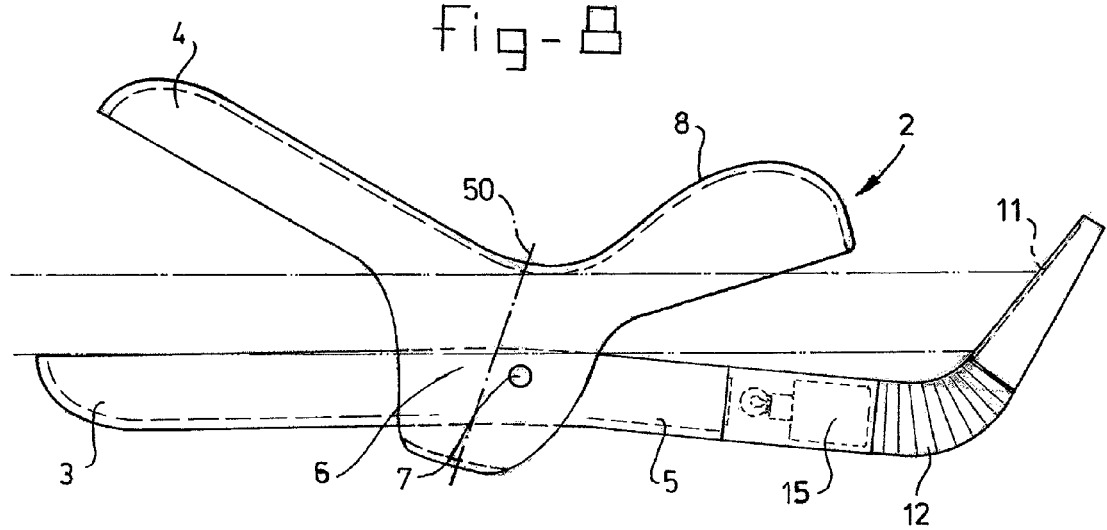

VAGINAL SPECULUM

CROSS REFERENCE TO RELATED APPLICATIONS

This application is a Divisional of U.S. patent application Ser. No. 10/451,066, which is a national stage of PCT Application No. PCT/NL00/00949 filed Dec. 22, 2000 and which claims benefit of Netherlands Application No. 1013958 filed Dec. 24, 1999, the entire disclosures of which are incorporated by reference.

BACKGROUND OF THE INVENTION

The invention relates to a vaginal speculum comprising two spoon blades which form a spoon blade assembly and:
- are intended for introduction into the vagina;
- are elongated; and
- are located alongside and opposite one another;
the one spoon blade at one end of the spoon blade assembly being provided with two bodies which together with said one spoon blade form a housing of essentially U-shaped cross-section and the other spoon blade being accommodated between said bodies such that it is hingeable with respect to the one spoon blade.

As is generally known, specula are used as a medical instrument by general practitioners, gynaecologists and currently to an increasing extent also by doctors' assistants (in the present text referred to below as the physician), for example to prepare smears and cultures and to investigate the positioning of contraceptive means, such as a coil.

The known specula have the disadvantages that they usually have ergonomics which are not woman-friendly, that operating handles and/or operating hands impede the view inwards and that the specula are not suitable for self-inspection.

The woman-unfriendly ergonomics are firstly revealed in the way in which a speculum is inserted. Insertion takes place by sliding the spoon blades in the closed position at an angle into the mouth of the vagina and then turning through a quarter turn. In practice, during this operation protruding operating handles or other external elements, as well as the physician's hand(s), come into contact with the back of the top of the thighs, the buttocks and/or other parts of the body of the woman, which is found to be unpleasant. Secondly, a speculum has two operating handles which are fixed to one another so that the spoon surfaces can be fixed—with some flexibility—in the spread position, after which the hold on operating handles of the speculum can be released. The woman also finds this fixed position unpleasant. Thirdly, it is difficult for the woman to "see what is going on" during the examination. This is because the ability to see is impeded by the position which she has assumed. It is more woman-friendly if the woman can follow the examination easily without additional effort. It is possible for the woman to view by means of a mirror which is fitted on the speculum or which is held and oriented by the physician or by the woman herself. In practice, however, this works only if the woman or the physician has two hands free for this. Furthermore, it is temporarily impossible for the examination to proceed because the mirror and/or the hands impede the physician's view inwards. In practice, the use of a mirror in this way results in a situation which is awkward and consequently unpleasant for the woman.

According to the prior art attempts are made to overcome the disadvantage that the operating handles and/or operating hands impede the view inwards during use by placing the operating handles at an angle of the order of magnitude of 30° to 60° to the spoon blades and/or making a sight opening in the spoon through which a view is obtained. However, this is even more disadvantageous with regard to woman-friendliness. After all, on the one hand the risk that the operating handles and the physician's hand come into contact with parts of the body of the woman when inserting the speculum increases as a result and, on the other hand, after the spoon blades have been fixed in the spread position the operating handles protrude at an angle with respect to the woman's body, which is found to be extremely unpleasant. Moreover, as a result of this positioning of the operating handles the woman is hardly able or unable to operate the operating handles herself. After all, in order to grasp these operating handles she would have to reach with one of her arms, wrist and hand in an unnatural and uncomfortable position from behind over one of her thighs, which in practice is hardly possible. Moreover, the woman still has to exert a squeezing movement on the operating handles, one side of which is in contact with her thigh or buttocks, as a consequence of which she still impedes the view inwards by her hand, wrist and/or lower arm, in any event during insertion and removal of the speculum, where it is important to have an unimpeded view inwards and of the mouth of the vagina.

Furthermore, specula known in the state of the art are found not to be suitable for self-inspection for one of more of the following reasons:

Firstly, the woman cannot support herself with one of her arms or hands during inspection because she needs both hands to operate the spoons and/or the retaining means which serve to fix the spoons with respect to one another.

Secondly—even if one hand suffices for operating the spoons—the operating hand has to assume a position which is unnatural, uncomfortable and impossible in practice.

Thirdly—even if one hand suffices for operating the spoons—the hand or operating handles block the view inwards while performing the squeezing movement that is necessary in order to be able to spread the spoon blades.

Fourthly, when inserting and operating the speculum the hand(s) impede(s) the view via the mounted mirror.

One or more of these disadvantages can be overcome to a greater or lesser extent by making use of a gynaecological chair, but in the case of self-inspection, for example at home, a gynaecological chair will not be available and the disadvantages therefore remain insurmountable.

A vaginal speculum of the type mentioned in the preamble is disclosed in, inter alia, DE-A 74,364, U.S. Pat. Nos. 3,324,850, 5,072,720 and 5,052,372. Such specula are in general introduced, or at least partially introduced, into the vagina in a position in which they are rotated relative to the longitudinal direction of the spoon blades and are then turned through 90° into a use position. The spoon blades then have to be spread and fixed in the spread position in order to hold the speculum in place in the vagina. When the spoon blades of the speculum have not yet been spread or have not yet been adequately spread, the speculum has to be held in place by the operating person with one hand, since the muscular tissue in the vagina exerts a force on the speculum which has been introduced which tends to expel the speculum. Once the spoon blades have been adequately spread, these spoon blades act as a resistance element that counteracts expulsion.

U.S. Pat. No. 3,769,980 discloses a speculum which has attachments of a flexible, or at least semi-flexible, material fitted on the ends of the spoon blades. When the spoon blades are spread these flexible attachments ensure that the vaginal wall assumes an arc-like shape (literally "vaulting") so that the cervix moves towards the mouth of the vaginal wall. However, this requires the hinge point about which the spoon blades hinge relative to one another to be a relatively long way outside the body in order to be able to stretch the mouth of the vagina to achieve the "vaulting" effect. This may be acceptable for performing an (early) abortion, but is uncomfortable for the patient and therefore undesirable for normal inspection purposes and taking smears.

SUMMARY OF THE INVENTION

The aim of the present invention is, firstly, to provide a vaginal speculum with greater ease of use and improved handling characteristics during use.

Said aim is achieved according to the invention in that the exterior of the U-shaped housing is shaped such that:

said housing can be accommodated in the mouth of the vagina after the spoon blades have been introduced into the vagina; and said housing, at least when the spoon blades are in a position in which they have essentially been brought together, can be held in place in the mouth of the vagina by the muscle tissue at, and in particular all round, the mouth of the vagina. The muscle tissue at the mouth of the vagina comprises in particular the musculus sphincter ani externus and the left-hand and right-hand parts of the musculus bulbocavernosus. The musculus bulbocavernosus, which forms part of the superficial muscles of the pelvic floor, is attached at the top to the pubic bone (symphisis pubis) and at the bottom is joined to the upper section of the musculus sphincter ani externus. The left-hand and right-hand parts of the musculus bulbocavernosus, together with the musculus sphincter ani externus, form a fleshy ring of muscle tissue surrounding the mouth of the vagina. This fleshy ring of muscle tissue is found to be able to hold the housing of the vaginal speculum according to the invention in place in the mouth of the vagina if said housing is of suitable size and shape. If said housing is of adequate size, it will be able to pass through the fleshy ring of muscle tissue only by stretching this fleshy ring of muscle tissue. As a consequence, when the housing is in the ring the fleshy ring of muscle tissue will exert a reactive force on the housing, which reactive force, in the case of a suitable shaping of the housing which will be obvious to those skilled in the art, will be directed essentially in the direction of introduction, that is to say into the vagina or towards the mouth of the uterus, and thus fixes the vaginal speculum in the mouth of the vagina instead of expelling the speculum again. It is also conceivable that the housing is so shaped and is arranged in such a position on the speculum that said housing passes through, or at least essentially passes through, the abovementioned fleshy ring of muscle tissue when the speculum is inserted, so that this ring first has to be stretched in order to remove the speculum from the vagina again and unintentional automatic expulsion of the speculum from the vagina is thus counteracted.

The specula known from the prior art have a housing that cannot be inserted, or cannot adequately be inserted, into the mouth of the vagina because of external projections and/or the housing or the speculum is provided with external surfaces which, viewed in the longitudinal direction of the speculum, diverge towards the outer end of the speculum and thus constitute an engagement surface for a force tending to expel the speculum, which force, as a consequence of the elastic properties of the vaginal tissue, is exerted on the speculum that has been introduced.

With regard to holding the speculum according to the invention in place in the mouth of the vagina it is pointed out that this can take place passively by stretching the muscle tissue in the mouth of the vagina and/or actively by tensioning of this muscle tissue, which can very readily be achieved by tensioning of the muscles of the pelvic floor.

The fact that the housing can be constructed in a wide variety of ways in order to achieve the retention effect sought according to the invention will be clear to a person skilled in the art, given the anatomy of the human body, and is, moreover, illustrated with reference to the illustrative embodiments given in the description of the figures. With this arrangement the essentially U-shaped housing can be open or closed at the free ends of the arms of the U. Furthermore, the essentially U-shaped housing can be partially open and partially closed, and the housing can also be so shaped that in the fixed position, ready for spreading, part of the housing protrudes from the vagina.

According to an advantageous embodiment of the invention, the underside of the housing is provided with at least one surface that tapers with respect to the longitudinal direction of the speculum in the direction of the external part thereof, on which surface the musculus sphincter ani externus and/or the musculus bulbocavernosus is able to act/engage when the speculum is in the position in which it has been inserted in the vagina and is ready for use, that is to say when the spoon blades are in the position in which they have been brought together (or when the spoon blades are in the unspread position), such that a compressive force pushing the speculum into the vagina is exerted on said tapering surface. In this context the underside of the housing relates to the position of the speculum when it is in the position ready for use, that is to say the position in which the spoon blades can be spread. If use is made of a U-shaped housing that is essentially open on the underside (that is to say a housing in the shape of an upside-down U), there will preferably be two such tapering surfaces, that is to say one tapering surface on the underside of each arm of the U.

According to a further advantageous embodiment of the invention, the at least one tapering surface can form part of an indentation made in the underside of the housing. With this arrangement this indentation will preferably have a shape matched to the upper contour of the musculus sphincter ani externus. The musculus ani externus is then able to engage in this indentation when the speculum is in the inserted position and thus hold the speculum in place. In this position, on the one hand, a compressive force directed towards the vagina will be exerted on the speculum and, on the other hand, a force directed out of the vagina will be exerted on the speculum, but because the musculus sphincter ani externus is in the indentation, a resistance counteracting expulsion of the speculum will be provided.

According to a further advantageous embodiment, the outside of the housing can be provided with a constriction extending over at least part of the periphery of the housing, in which constriction muscle tissue extending around the mouth of the vagina is able to engage when the speculum has been inserted in the vagina and is in the position ready for spreading. Just as in the case of the embodiment with the indentation which has been discussed above, with this arrangement a resistance counteracting expulsion is provided because the muscle tissue is able to nestle as it were like a tautly stretched cord in the constriction. Preferably, the constriction will extend over the entire periphery of the housing.

The housing of a vaginal speculum according to the invention can in principle assume a wide variety of shapes, but, with a view to the anatomy of the female body, will preferably have a profile that is oval in cross-section and that optionally can be open at the ends of the bodies facing away from the one spoon blade.

According to a further advantageous embodiment, the vaginal speculum according to the invention is provided with only a single operating handle, which, when the speculum has been inserted, forms an extension of the other spoon blade protruding to the outside. Only one hand is needed to operate such a vaginal speculum, which hand, moreover, can very easily be a hand of the woman in whom the speculum has been or is being inserted. Because this woman needs only one hand to insert and operate the speculum herself and this hand is able to clasp the operating handle in a manner that is natural and easy for the body, the other hand can remain available for support, as a result of which it is possible for the user to perform a self-inspection.

In general, it can be stated in this context that a speculum is suitable for self-inspection if it is made possible for the user to insert and to operate the speculum with one hand without the assistance of others and preferably at the same time has an unimpeded view inwards into the spreading/spread body cavity, in this case the vagina.

Especially in the case of self-inspection, operation of the speculum is appreciably facilitated if the one spoon blade is the upper spoon blade, that is to say if the other spoon blade provided with an operating handle is the lower spoon blade, so that the operating handle merely has to be pulled upwards in order to spread the spoon blades, which the user, that is to say the woman carrying out a self-inspection, is easily able to carry out using one or two fingers.

In order to facilitate self-inspection, it is furthermore advantageous according to the invention if the operating handle is provided with optionally detachable mirror means which are directed or can be directed such that the woman in whom the speculum has been inserted is able to see the interior of the vagina when the spoon blades are spread. However, it must be pointed out that such an embodiment is particularly suitable not only for self-inspection but also in the case of inspection by, for example, a gynecologist or general practitioner since in that case also it is possible for the patient then to be able to see together with the gynecologist or general practitioner during inspection of the vagina.

In order further to facilitate self-inspection or inspection by a physician, it is advantageous according to the invention if the operating handle is provided with optionally detachable lighting means oriented in the direction of the spoon blades. With this arrangement it is readily possible to position the light source outside the region required for an inward view and to guide the light inwards via a light guide, which optionally is able to follow a bend. Such a light guide can be a hose or tubular element or mirrors, but can also be a solid, transparent body that directs the light along a path.

According to a further advantageous embodiment the vaginal speculum according to the invention can be provided with means for holding it open to fix the spoon blades in a spread position. Such means for holding it open can be implemented in a wide variety of ways. In particular, said means according to the invention for holding the speculum open can comprise a ratchet mechanism that allows spreading of the spoon blades from the one discrete spread position to a more widely spread discrete spread position and impedes closing of the spoon blades. Of course, an unlocking mechanism will usually also be provided with this arrangement in order to be able to disable the ratchet mechanism or to close the spoon blades again.

The spoon blades of a speculum according to the invention can assume a wide variety of shapes known per se from the prior art, such as a shape that is essentially U-shaped in cross-section, the concave sides of the spoon blades facing one another, which embodiment is also referred to by the term "duck's bill".

In order to facilitate assembly of the vaginal speculum according to the invention and removal of the vaginal speculum according to the invention from the vagina in the case of unforeseen circumstances rendering removal more difficult, it is advantageous according to the invention if the other spoon blade is detachably accommodated between the bodies on the one spoon blade by means of a pin-and-slot linkage made in each body, the pins thereof defining the hinge axis for hinging of the other spoon blade with respect to the one spoon blade, whilst the slots thereof are oriented such that the other blade can be detached from the bodies by pulling said other spoon blade away in a direction which roughly is opposite to the direction of insertion of the speculum.

With a vaginal speculum according to the invention it is possible to provide a speculum suitable for self-inspection, with which the woman is herself able to check the mouth of her uterus, her vaginal wall and/or the positioning of contraceptive means without the intervention of a general practitioner, gynecologist or other person.

The speculum according to the invention can be inserted in its longitudinal direction, with the spoon blades in the closed position and tilted through 90° with respect to the position ready for spreading, into the mouth of the vagina by the user herself and then turned through a quarter turn in order then to be slid in further until the housing is held in place by the muscle tissue located at the mouth of the vagina. With this arrangement the housing is preferably arranged on the spoon blade that is located on the side of the pubic bone when the speculum is in use, the operating handle then preferably being arranged on the other spoon blade. With this arrangement the spoon blades are essentially parallel with respect to one another, at least in the closed position thereof. There is no need for any protruding elements, or hands of a third party, that come into contact with the woman's body during introduction.

Because the speculum is and remains held in place once it has been introduced into the mouth of the vagina, even when the spoon blades have not been spread (which is a specific requirement for retention in the case of the specula known from the prior art), the setting of a specific spread position can be dispensed with. This makes the speculum according to the invention extremely suitable for self-inspection and furthermore appreciably increases the ease of use, including use by a physician. When the spoon blades of the speculum according to the invention are spread, these spoon blades are then able, in the spread position, optionally to take over or cancel out retention by means of the housing of the speculum, but when the spoon blades are closed again the housing will then again ensure retention of the vaginal speculum. Locking in the spread position, which usually is found to be very unpleasant by the woman in whom the speculum has been inserted, can thus be completely avoided.

Because the user needs only one hand to insert and operate the speculum and this hand is able to clasp the operating handle in a manner that is natural and easy for the body without impeding the view through the sight opening in the speculum and/or via the optionally attached mirror means, she herself—and the physician who may be present—is/are able to carry out the examination easily without interruptions.

Because with the speculum according to the invention the help of a third party is not needed in order to introduce the speculum into a woman, to turn it and to operate it, it is possible in the case of inspection by a physician as far as possible to restrict the bodily contact with that physician, which is frequently found to be unpleasant.

BRIEF DESCRIPTION OF THE DRAWINGS

The present invention will be illustrated in more detail below with reference to the appended drawing in which a few illustrative embodiments have been developed.

In the drawings:

FIG. 3 shows a diagrammatic side view of a further embodiment of the vaginal speculum according to the invention;

FIG. 4 shows a diagrammatic side view of yet a further embodiment of a vaginal speculum according to the invention;

FIG. 5 shows a rear view of part of the vaginal speculum according to FIG. 4;

FIG. 7 shows a diagrammatic side view of the vaginal speculum from FIG. 6 in the closed position; and FIG. 8 shows the vaginal speculum from FIG. 7 in the spread position.

DETAILED DESCRIPTION OF THE INVENTION

Figure 1:
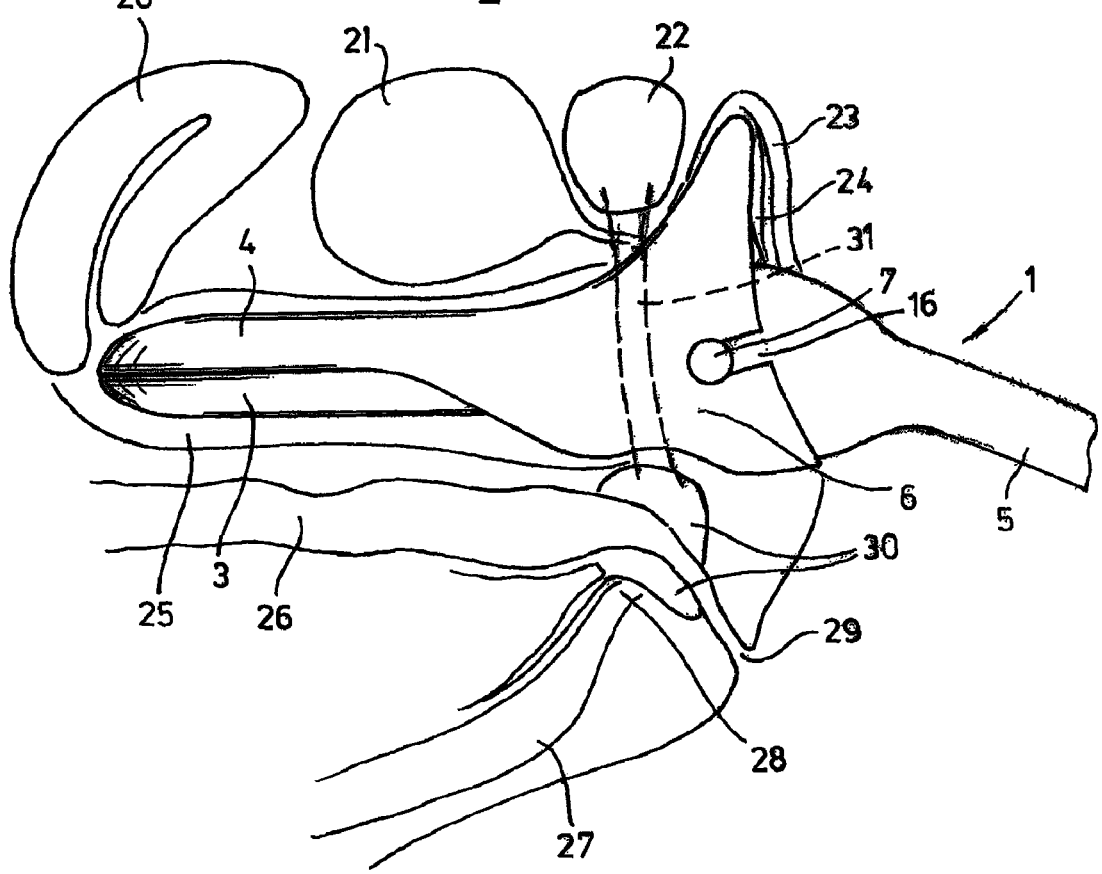
FIG. 1 shows, diagrammatically, a cross-section of the female body at the location of the vagina with a view of a vaginal speculum according to the invention inserted therein.

In the figures the same reference numerals have been used for corresponding components in the various embodiments.

FIG. 1 shows a side view of a vaginal speculum 1 according to the invention introduced into a vagina, the surroundings of which are shown in cross-sectional view. With regard to the surroundings of the vagina it is pointed out that 21 indicates the bladder, 22 the pubic bone (symphysis pubis), 23 the major labia (labium majus), 24 the minor labia (labium minor), 25 the vagina, 26 the rectum, 27 the sacrum, 28 the coccyx (os coccygis), 29 the anus, 30 the anal sphincter (musculus sphincter ani externus) and 31 the musculus bulbocavernosus.

Figure 2:
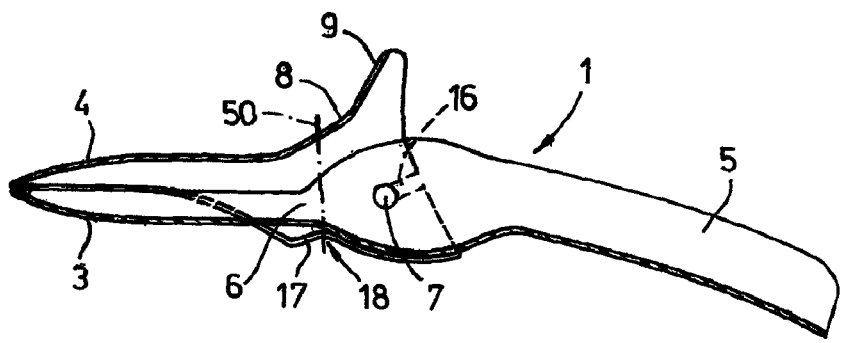
FIG. 2 shows a mid longitudinal section of the vaginal speculum from FIG. 1.

FIG. 1 further shows a speculum 1 according to the invention, comprising a lower spoon blade 3, an upper spoon blade 4 and an external operating handle 5. FIG. 2 shows a mid longitudinal section of this speculum 1. The plane of intersection of this mid longitudinal section is also a mirror symmetrical plane of the speculum 1. The upper blade 4 is provided with bodies 6 at one end of the spoon blade assembly 3, 4, the so-called outward-facing external end thereof, which bodies 6, together with said spoon blade, form a housing that is essentially U-shaped in cross-section and that is open at the bottom in order to make wide spreading of the spoon blades possible. The upper spoon blade 4 has a contact surface 8 at the so-called external end, the external shape of which contact surface 8 is matched to the shape of the vagina in the vicinity of the pubic bone. The lower spoon blade 3 is accommodated between the bodies 6 by means of a pin 7-and-slot 16 linkage such that it is hingeable with respect to the upper spoon blade 4. It will be clear that the pin-and-slot linkage 7, 16 makes it possible for the lower spoon blade 3 to be removed from the housing formed by the bodies 6 and the upper spoon blade 4 (including its contact surface 8) in a direction opposite to the direction for introduction of the speculum into the vagina.

As is illustrated in FIG. 1, there is a fleshy ring of muscle tissue, consisting of the left-hand and right-hand parts of the musculus bulbocavernosus 31 and the musculus sphincter ani externus 30, at the mouth of the vagina. The musculus bulbocavernosus 31 is attached at the top to the pubic bone 22 and at the bottom is joined to the musculus sphincter ani externus 30. This fleshy ring 30, 31, 50, 51 of muscle tissue delimits the mouth of the vagina all round and on tensioning will hold the speculum 1 according to the invention in place in the vagina. This tensioning can take place passively by stretching the fleshy ring 31, 30 of muscle tissue using the housing of the speculum and/or actively by tensioning of the muscle tissue of the fleshy ring 30, 31, for example by tensioning of the muscles of the pelvic floor. The bottom edges of the bodies 6 are each provided with a recess 18 in which the musculus bulbocavernosus is able to engage. The shape of this recess 18 will preferably be matched to the shape of the top of the ani externus 30. The sloping flat section 17 of the recess 18, which sloping flat section 17 tapers in the longitudinal direction towards the external end of the speculum and in the direction of the longitudinal axis, provides a contact surface via which the musculus bulbocavernosus is able to exert a compressive force on the speculum, directed into the vagina. However, it will be clear that in the case of the indentation 18 retention also takes place because the musculus bulbocavernosus nestling herein provides resistance to movement of the speculum in the longitudinal direction.

In FIG. 2 the position of the fleshy ring of muscle tissue during use is indicated diagrammatically by a centre line 50.

FIG. 3 shows, highly diagrammatically, a highly simplified, further embodiment of a speculum 41 according to the invention. The speculum comprises a spoon blade 3 and, respectively, 4, that extends into the body cavity during use, an external part 5 that extends outside the body cavity during use and a part 6 that can extend outside or at least partially inside the body cavity during use. The spoons 3 and 4 are fixed to one another via a hinge pin 8. With a view to an unimpeded field of view between the connection points of the spoons 3 and 4, the hinge pin 7 is preferably a hinge, for example a pin linkage, on either side of the bodies by means of which the spoon blades 3 and 4 are fixed to one another. In the shown, closed position of the spoons, the spoon blades 3 and 4 are essentially in contact with one another. There can be a small gap between the spoon blades 3 and 4 in order to prevent tissue from becoming trapped between the two spoon blades when these move from the spread position into the closed position. Furthermore, the speculum has one operating handle 5. The bodies 6, together with the upper spoon blade 4, form the housing. The upper spoon blade also has a contact surface 8 that during use is placed in contact with the body at the location of the pubic bone. Mirror means 11 and lighting means 15 are fitted on the operating handle 5 by means of a unit 12 that can be slid up and down. Both means can be detachable and/or adjustable if desired. In FIG. 3 the fleshy ring of muscle tissue is indicated diagrammatically by the dash-and-dot line 50. Each arm 6 and/or the top of the spoon blade 4 is provided with a constriction/indentation 52 (for the arms 6) and, respectively, 53 for the top of the spoon blade. If both the arms 6 and said top of the spoon blade 4 are provided with a constriction/indentation, the complete constriction/indentation will be U-shaped over the entire U-shaped housing. Because the fleshy ring of muscle tissue 50 engages in the constriction 52 and/or 53, the speculum automatically remains held in position, at least when it has been introduced.

In FIG. 4 the embodiment according to FIG. 3 is expanded by means 13 for holding it open, which means 13 extend between the spoons 3 and 4 in order to hold these in the spread position so that the user can have both hands free. Spring means 14 which extend between the spoon blades 3 and 4 can optionally be provided in order to force the spoons into the closed position, and to hold them in this position, when at rest. These means for holding the spoons open and spring means can be detachable, if desired. Furthermore, another embodiment of the contact surface 8 is shown in FIG. 4. The contact surface 8 forms part of the spoon blade 4. In sectional side view, the contact surface 8 has a shape which essentially corresponds to that of the body surface close to the pubic bone. In this way the force that is exerted on the body by the body rest 6 when the speculum is used is distributed over a larger surface area, which results in a lower average pressure which the user is better able to bear.

With regard to holding in place by the fleshy ring 50, yet a further variant is shown in FIG. 4. The constrictions 52 and 53 from FIG. 3 are also indicated by broken lines in FIG. 4 as an additional variant thereto, it once again being the case that these constrictions 52 and 53 can be provided "and/or". The further variant for holding in place makes use of constrictions 54 and/or 55. Constrictions 54 are formed in the bottom edge of the arms 6. Constriction 55 is formed in the underside of spoon blade 3. If constriction 55 is absent, the arms 6 will, in the position of the spoon blades shown in FIG. 4, extend to below spoon blade 3 in order to make the constrictions 54 accessible to the fleshy ring of muscle tissue 50. If the constrictions 54 are absent, it is preferable that the bottom edges of the arms 6 extend no further than the highest point of the constriction 55.

FIG. 5 shows a particular embodiment of the contact surface 8 which now has two lip-shaped parts 9, between which parts there is an opening 10. By means of this shape of the contact surface 8, which is essentially V- or U-shaped when viewed from the front, it is possible to prevent the contact surface 8 coming into contact with the urethra and compressing this, which would be painful, when the speculum 42 is used. The contact surface 8 can be positioned by the user in contact with her body at the location of her pubic bone in such a way that the urethra will be at the location of the opening 10. The lip-shaped parts 9 are positioned in the area of the user's groin.

Figure 6:
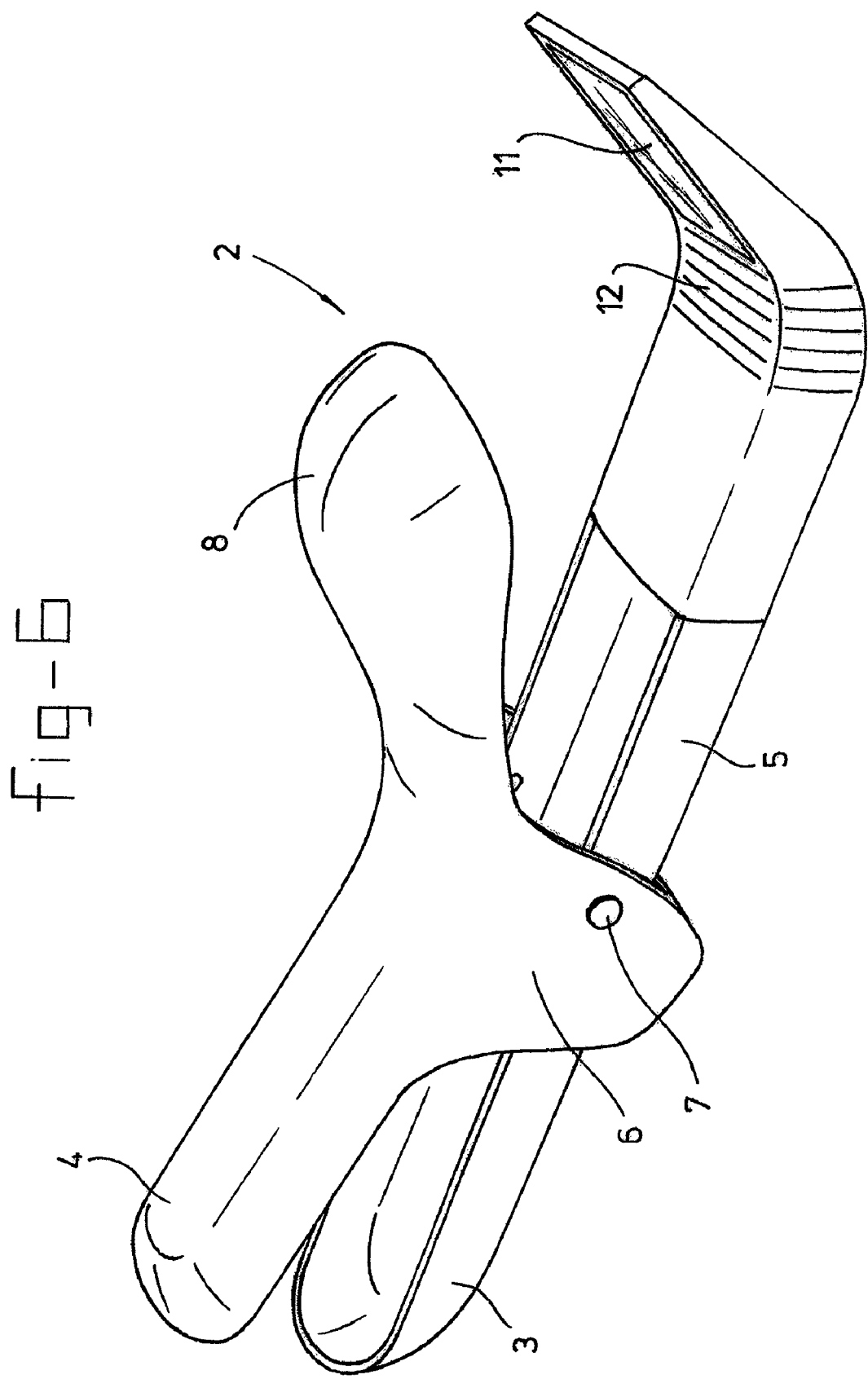
FIG. 6 shows a perspective view of yet a further embodiment of a vaginal speculum according to the invention.

Yet a further embodiment 2 of the speculum according to the invention is shown in FIGS. 6, 7 and 8, which embodiment appears to be more practical than that in FIGS. 3 and 4. This speculum 2 comprises two spoon blades 3 and 4 and an operating handle 5 that forms an extension of the spoon blade 3. The spoon blades 3 and 4 are essentially U-shaped in cross-section. On either side of the speculum the spoon blades 3 and 4 are hingeably joined to one another via bodies 6 by means of a hinge 7, for example a pin or nail hinge. The bodies 6 are arranged on the spoon blade 4 that during use is on the side of the pubic bone and the operating handle 5 is arranged on the other spoon blade 3. The bodies 6 form an integral whole with the spoon blade 4, that further has a contact surface 8 that when viewed from the side in section has a shape that essentially corresponds to that of the body surface close to the pubic bone. The spoon 3 can, for example approximately at the location of the hinges 7, have a kink such that in the insertion position the handle 5 bends away downwards and this handle 5 leaves more room for inward vision, or is less in the way, when the speculum is in the spread position. This promotes an unimpeded and broad field of view over the spoon concerned. A holder 12 with mirror 11 fitted is mounted on the exterior part 5, which holder 12 can be detachable. Furthermore, lighting means 15 can be arranged in the holder 12. The mirror 11 can optionally be adjustable.

FIG. 7 shows the speculum 2 in the embodiment according to FIG. 6 in the closed position.

FIG. 8 shows the speculum 2 in the embodiment according to FIGS. 6 and 7 in the spread position. The field of view is determined by the position of the mirror 11, which is adjustable, and the rotation of the spoon 3 about the hinge pin 7 with respect to the other spoon 4. A wide area can be viewed by rotating the spoon 3 to a greater or lesser extent relative to the spoon 4. The user is able to adjust the view via the mirror to the one she requires by adjusting the position of the mirror 11.

In FIGS. 6, 7 and 8 it can clearly be seen that the housing at least partially has a closed oval shape. After the speculum has been introduced, the mouth of the vagina will be in the position of this region of oval cross-section, as is indicated by centre line 50 approximately at the location of the hinges 7 which then, for example, are just inside the body cavity.

With regard to the embodiment of the speculum 41 according to FIG. 3, it is pointed out that this speculum can be retained in the mouth of the vagina when the fleshy ring of muscle tissue, as is shown by the centre line 50, encloses, under tension, the bodies 6, the contact surface 8 and that part of the bottom of spoon blade 3 that is located opposite the contact surface 8. With this arrangement this tensioning of the fleshy ring of muscle tissue 50 can be achieved by active tensioning of the muscles of the pelvic floor, but also because the dimensions of the housing are somewhat larger than the passage surrounded by the fleshy ring of muscle tissue in the relaxed state. As a consequence of the shaping of the speculum (such as the constrictions 52 and/or 53 and/or 54 and/or 55) at the location of the fleshy ring 50 of muscle tissue, this ring 50 will not exert a force on the speculum that tends to expel the speculum. With the aid of the centre line 51, it is further indicated in FIG. 3 that it is also conceivable that the so-called housing is slid beyond the fleshy ring of muscle tissue, in this case indicated by centre line 51. It will be clear that in this case also the fleshy ring 51 of muscle tissue will not be able to exert an expelling force on a speculum that has been introduced.

With regard to the embodiment of the speculum 42 according to FIGS. 6, 7 and 8, it is pointed out that with this embodiment retention of the speculum when the spoon blades 3 and 4 have been squeezed together is achieved by the sloping flat part 17 tapering in the external direction of the speculum and towards the longitudinal axis thereof. When the fleshy ring 50 of muscle tissue is under tension in the manner indicated above, this ring 50 will exert a force on the speculum 2 acting in the direction of introduction.

Furthermore, it will be clear to an average person skilled in the art from the illustrative embodiments shown in the figures that retention of the speculum in the vagina is improved when the spoon blades 3 and 4 are adequately spread, or that the spoon blades then themselves completely take over the retention function from the housing on which the fleshy ring of muscle tissue engages. Such retention of a speculum in the vagina by spreading the spoon blades is known per se.

It is also readily conceivable to construct the housing on which the fleshy ring 50 of muscle tissue engages of variable size. This can be achieved, for example, by constructing the housing of two U-shaped components which are inserted in one another with the arms facing one another and are slideable relative to one another in the longitudinal direction of the arms.

As will be clear from the embodiments shown in the figures and the associated description, it is preferable according to the invention if the hinge axis in respect of which the one spoon blade and other spoon blade are hingeable with respect to one another is inside, optionally just inside, the mouth of the vagina when the speculum has been introduced. The reason for this is that the mouth of the vagina, in particular the fleshy ring of muscle tissue, is then stretched only slightly or is not stretched when the spoon blades are spread, which is beneficial for user friendliness.

As will furthermore be clear from the embodiments shown in the figures and associated description, it is preferable if the so-called other spoon blade is essentially entirely inside the bodies of the U-shaped housing, at least when the spoon blades are folded together, such as in the position during introduction. The bottom surface of said other spoon blade can optionally run just below the (free) ends of the arms. The advantage of this is that the mouth of the vagina, in particular the fleshy ring of muscle tissue, is stretched to only a slight extent or even is not stretched at all when the spoon blades are spread, which is beneficial for user friendliness.

Stretching of the fleshy ring of muscle tissue to only a slight extent or not at all also benefits the reliability of the retention of the speculum therein, since the risk of expelling is lower. In order to ensure that the fleshy ring of muscle tissue is not stretched at all when spreading the spoon blades, it is advantageous if the U-shaped housing is essentially closed at the free ends of the arms of the U.

Finally, it is pointed out that it will be clear to an average person skilled in the art where the housing has to be arranged on the speculum and how this housing can be dimensioned in order to achieve the self-retaining effect according to the invention.

What is claimed is:

1. Vaginal speculum comprising:
   two spoon blades which form a spoon blade assembly configured to be introduced into a vagina, said spoon blades being elongated and position substantially alongside and opposite each other,
   wherein the one spoon blade at one end of the spoon blade assembly comprises two bodies to form a housing of essentially U-shaped cross-section and the other spoon blade is hingeable with respect to the one spoon blade around a hinge axis,
   wherein the speculum has a closed state when the spoon blades are in a position in which they have been brought together and a opened state when the blades are spread at an internal end of the speculum,
   wherein the exterior of the U-shaped housing is shaped for accommodating said housing in the mouth of the vagina after the spoon blades have been introduced into the vagina,
   wherein the housing is provided with at least one surface that tapers in the closed state and the opened state, with respect to the longitudinal direction of the speculum in the direction of the external part thereof; said tapering surface for holding said housing in place, in both the closed state and opened state, in the vagina by the musculus sphincter ani externus and/or the musculus bulbocavernosus is able to act/engage when the speculum is in the position in which it has been inserted in the vagina and is ready for use, such that a compressive force pushing the speculum into the vagina is exerted on said tapering surface,
   wherein said hinge axis is arranged such that, when the speculum is inserted into the vagina, said hinge axis lies inside the mouth of the vagina, and
   wherein the at least one tapering surface forms part of an indentation made in the housing.

2. Vaginal speculum according to claim 1, wherein the speculum comprises a contact surface for contacting the female body, said contact surface being located more external from said hinge axis.

3. Vaginal speculum according to claim 1, wherein the outside of the housing is provided with a constriction extending over at least part of the periphery of the housing, in which constriction muscle tissue extending around the mouth of the vagina is able to engage when the speculum has been inserted in the vagina and is in the position ready for use.

4. Vagina speculum according to claim 2, wherein a distance between the contact surface and the tapered surfaces approximately equal to an average distance between the ring of muscle tissue extending around the mouth of the vagina and an exterior part of the vagina.

5. Vaginal speculum according claim 1, wherein the housing has a profile that is oval in cross-section and that can be open at the ends of the bodies facing away from the one spoon blade.

6. Vaginal speculum according claim 1, further comprising a single operating handle, which, when the speculum has been inserted, forms an extension of the other spoon blade protruding to the outside, wherein one spoon blade is the upper spoon blade and in that the operating handle is provided with, optionally detachable, mirror means which are directed such that the woman in whom the speculum has been inserted is able to see the interior of the vagina when the spoon blades are spread.

7. Vaginal speculum according to claim 6, wherein the operating handle is provided with optionally detachable lighting means oriented in the direction of the spoon blades.

8. Vaginal speculum according to claim 2, wherein the one spoon blade is the upper spoon blade which comprises the contact surface, the shape of which essentially corresponds to the body surface in the mouth of the vagina close to the pubic bone.

9. Vaginal speculum according to claim 7, wherein the contact surface has two lip-shaped parts extending roughly in the longitudinal direction of the speculum with an opening between them for accommodating the urethra or the mouth thereof.

10. Vaginal speculum according to claim 1, further comprising means for holding the spoon blades in an open, spread position, wherein said means for holding open comprise a ratchet mechanism that allows spreading of the spoon blades from the one discrete spread position to a more widely spread discrete spread position and impedes closing of the spoon blades.

11. Vaginal speculum according to claim 1, wherein the spoon blades are essentially U-shaped in cross-section, the concave sides of the spoon blades facing one another.

12. Vaginal speculum according to claim 1, wherein the other spoon blade is detachably accommodated between the bodies on the one spoon blade by means of a pin-and-slot linkage made in each body, the pins thereof defining the hinge axis for hinging of the other spoon blade with respect to the one spoon blade, whilst the slots thereof are oriented such that the other spoon blade can be detached from the bodies by pulling said other spoon blade away in a direction which roughly is opposite to the direction of insertion of the speculum.

13. Vaginal speculum according to claim 1, wherein as viewed in longitudinal direction of the spoon blades and when the spoon blades are folded together, the other spoon blade lies essentially entirely inside the bodies of the U-shaped housing.

14. Vaginal speculum according to claim 1, wherein said housing is shaped and sized for passing said ring of muscle tissue only by stretching it during insertion.

15. Vaginal speculum according to claim 1, wherein the housing has in cross-section an oval shape in the region that lies, when the speculum is inserted in the vagina, inside the ring of muscle tissue.

16. Vaginal speculum according to claim 1, wherein the one spoon blade is the upper spoon blade and the other blade is accommodated between said bodies and wherein the hinge axis extends between said bodies transverse to the longitudinal direction of the speculum.

17. Vaginal speculum according to claim 1, wherein the contact surface has two lip-shaped parts extending roughly in the longitudinal direction of the speculum with an opening between them for accommodating the urethra or the mouth thereof.

18. Vaginal speculum according to claim 1, wherein the indentation is made in an underside of the housing.

19. Vaginal speculum according to claim 18, wherein the indentation is made in the upper spoon blade.

20. Vagina speculum according to claim 3, wherein the tapering surface forms part of the constriction.

* * * * *